United States Patent [19]

Zhou

[11] Patent Number: 5,871,482
[45] Date of Patent: Feb. 16, 1999

[54] BIONIC CERVIX UTERI DILATOR

[76] Inventor: Jingren Zhou, 3rd Fl., Ren Wei Science & Technology Bldg., Shi Hua Xi Road, Ji Da, Zhu Hai City, Guang Dong, P.R., China

[21] Appl. No.: 873,770

[22] Filed: Jun. 12, 1997

[30] Foreign Application Priority Data

Jun. 18, 1996 [CN] China ............................. 96 2 37079.7
Jun. 18, 1996 [CN] China ............................. 96 1 19088.4
Nov. 21, 1996 [CN] China ............................. 96 1 19184.8

[51] Int. Cl.$^6$ ................................................. A61B 17/38
[52] U.S. Cl. .............................. 606/34; 606/42; 600/548
[58] Field of Search ............................... 606/41, 42, 34, 606/32, 237; 600/548, 14

[56] References Cited

U.S. PATENT DOCUMENTS 4,052,978 10/1977 Eugenio .................................. 600/548
4,994,016  2/1991 Atwood ...................................... 600/14

*Primary Examiner*—Michael Buiz
*Assistant Examiner*—Julian W. Woo
*Attorney, Agent, or Firm*—Beveridge, DeGrandi, Weilacher & Young, LLP

[57] ABSTRACT

A bionic cervix uteri dilator comprises a power supply circuit, an oscillating circuit, a voltage step-up circuit and curing electrodes, wherein the output terminal of the power supply circuit is connected to the input terminal of the oscillating circuit the output terminal of the oscillating circuit is connected to the input terminal of the voltage step-up circuit, and the output terminal of the voltage step-up circuit is connected to the curing electrodes. The present invention has advantages of novel structure, safety and reliability. With a narrow pulse of frequency 1–200 Hz (being preferably selected from 5 to 150 HZ, further being preferable in between 5–50 HZ.) outputted on the output terminal, the cervix uteri can be effectively dilated by stimulating ear acupoints, so that gynecological diseases treatments can be facilitated, and the pains caused by cervical dilating by the use of instruments can be alleviated. The present invention is worth widely popularizing and utilizing.

20 Claims, 4 Drawing Sheets

BIONIC CERVIX UTERI DILATOR

FIELD OF THE INVENTION

The present invention relates to a bionic cervix uteri dilator.

BACKGROUND OF THE INVENTION

Generally, cervix uteri dilation is required in induced abortion and intrauterine treatment, and instruments are always needed in cervix uteri dilation, which may cause severe pain to the patient and make the operation of the doctor complicated and tedious.

Therefore, it is an object of the present invention to provide a bionic cervix uteri dilator capable of achieving cervical dilation by stimulating the acupoints (acupuncture points) of the human body.

SUMMARY OF THE INVENTION

The bionic cervix uteri dilator according to the present invention comprises a power supply circuit, an oscillating circuit a step-up transformer circuit and curing electrodes, wherein the output terminal of the power supply circuit is connected to the input terminal of the oscillating circuit, the output terminal of the oscillating circuit is connected to the input terminal of the step-up transformer circuit, and the output terminal of the voltage step-up circuit is connected to the curing electrodes.

BRIEF DESCRIPTION OF THE DRAWINGS

Further features and advantages of the invention will be best understood from the detailed description of some preferred embodiments of a bionic cervix uteri dilator with reference to the accompanying drawings, in which.

DETAILED DESCRIPTION OF THE INVENTION

Figure 1:
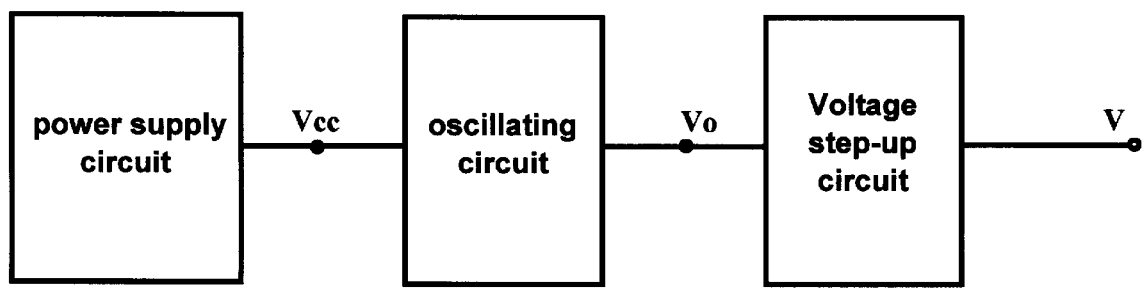
FIG. 1 is a schematic circuitry block diagram of the present invention.

Referring to FIG. 1, a bionic cervix uteri dilator of the present invention comprises a power supply circuit, an oscillating circuit and a set-up transformer circuit, wherein the output terminal of the power supply circuit is connected to the input terminal of the oscillating circuit, and the output terminal of the oscillating circuit is connected to the input terminal of the step-up transformer circuit.

Figure 2:
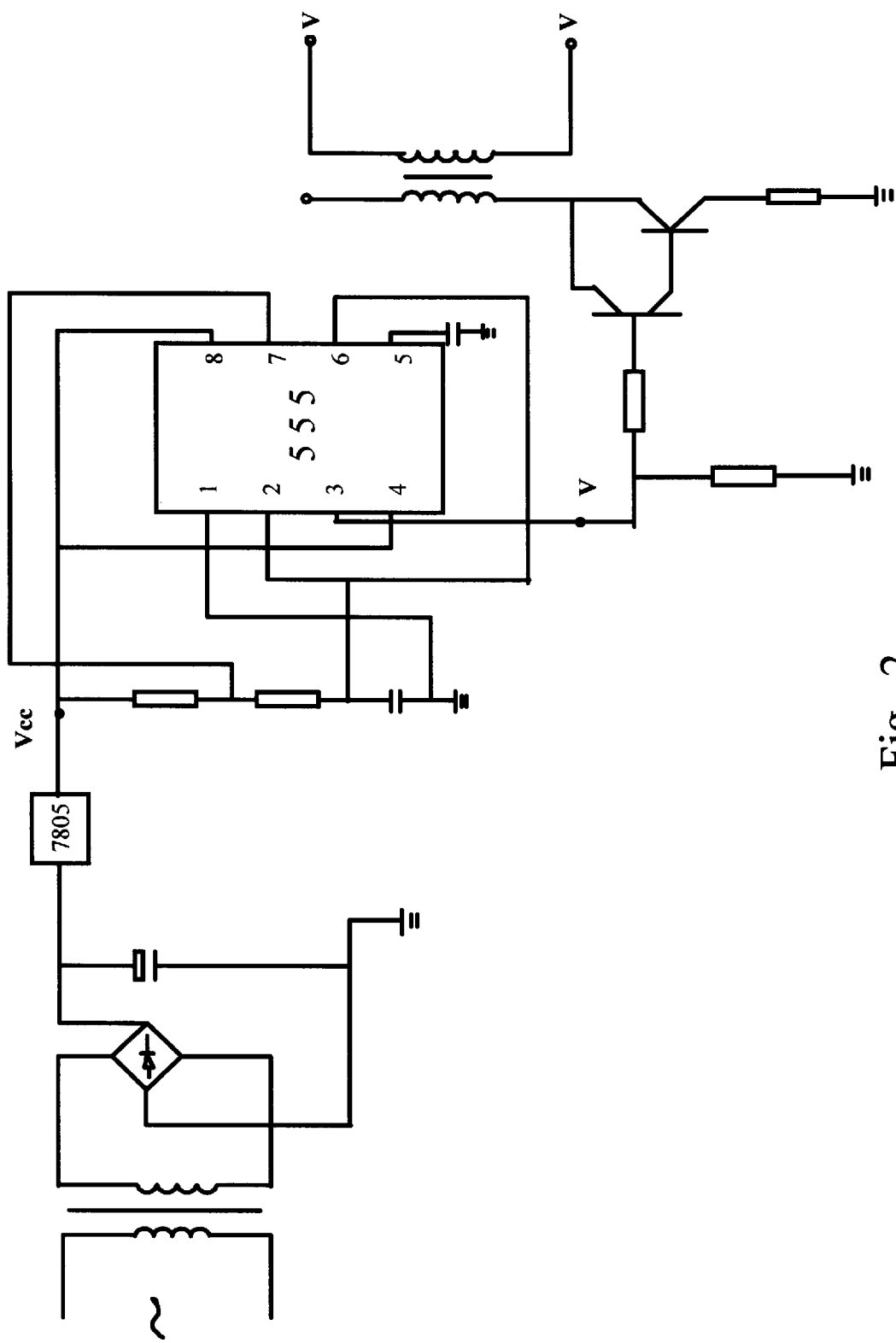
FIG. 2 is a schematic circuitry diagram of an embodiment of the present invention.

Referring to FIG. 2, the power supply circuit comprises a transformer, a bridge rectifier, a power supply voltage stabilizer and capacitors, wherein the electric-network voltage is stepped down by the transformer, rectified by the bridge rectifier, stabilized by the voltage stabilizer and outputted via the output terminal; the oscillating circuit comprises a chip (555), resistors and capacitors, wherein pin (1) of the chip (555) being grounded, pin (7) being connected to a resistor, pins (2 and 6) being connected in parallel with a resistor and a capacitor after connected in parallel with each other, pins (4 and 8) being connected to the output terminal (Vcc), pin (5) being grounded through a capacitor, and pin (3) being the output terminal (Vo); the step-up transformer circuit comprises resistors, transistors, and a transformer, wherein the base electrode of a transistor being connected to the output terminal (Vo) via a resistor, the collector of the transistor being connected to the primary coil of the transformer, the secondary coil of the transformer being the output terminals (V) connected with the curing electrodes, a narrow pulse of frequency 1–200 Hz being outputted on the output terminal (V). Said frequency of the narrow pulse can be preferably selected from 5 to 150 Hz, in which it is preferable in between 5–50 Hz.

Figure 3:
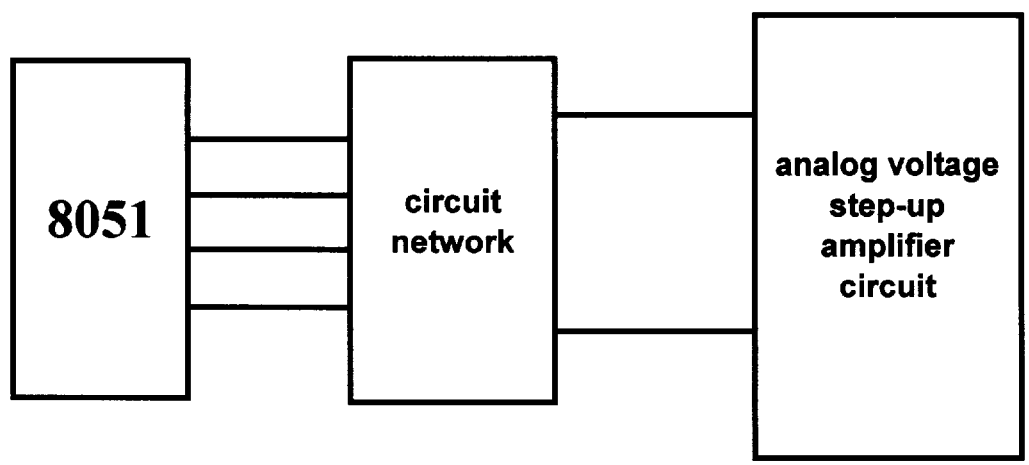
FIG. 3 is a schematic circuitry block diagram of other embodiment of the present invention.

Referring to FIG. 3, the principle of a bionic cervix uteri dilator of the present invention can also be implemented optionally with digital circuits such as chip (8051) circuit network, analog amplifier step-up circuit, etc., wherein the output terminal of the chip (8051) is connected to the input terminal of the circuit network, the output terminal of the circuit network is connected to the input terminal of the analog amplifier step-up circuit, and the output terminal of the analog amplifier step-up circuit is connected to the curing electrodes.

Figure 4:
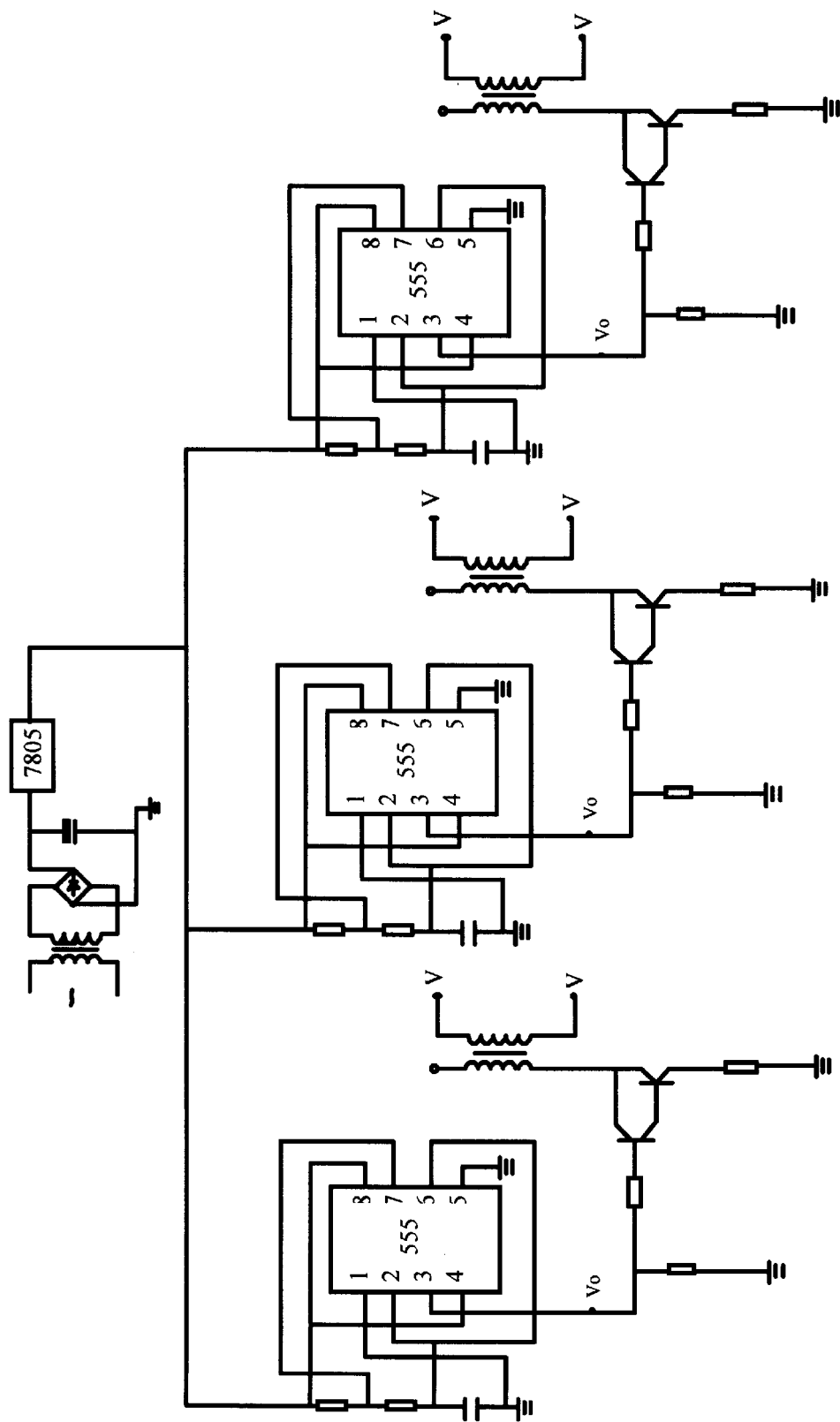
FIG. 4 is a schematic circuitry diagram of other embodiment of the present invention shown as FIG. 3.

Referring to FIG. 4, a power supply circuit comprises a transformer, a bridge rectifier, capacitors and a power supply stabilizer, the input terminals of a plurality of oscillating circuit are connected in parallel to the output terminal of the power supply circuit, each of the oscillating circuits comprises a chip (555), resistors and capacitors, the connecting scheme is similar to that of embodiment 1,shown as FIG. 3, that is, pin (1) of chip (555) being grounded, pin (7) being connected to a resistor, pins (2 and 6) being connected in parallel with a capacitor after connected in parallel with each other, pins (4 and 8) being connected to the output terminal (Vcc), pin (5) being grounded via a capacitor, and pin (3) being the output terminal (Vo); the step-up transformer circuit comprises resistors, transistors, and a transformer, the base electrode of a transistor being connected to the output terminal (Vo) via a resistor, the collector of the transistor being connected to the primary coil of the transformer, the secondary coil of the transformer being the output terminal connected with the curing electrodes, thus forming a plurality of curing voltage output terminals. Thereby, with one cervix uteri dilator, a plurality of acupoints of the human body can be acted on separately by the use of a plurality of pairs of electrodes simultaneously, without the common electrical apparatus zero point and interactions among the electrodes; a narrow pulse of frequency 1–200 Hz is outputted on the output terminal (V). Said frequency of the narrow pulse can be preferably selected from 5 to 150 Hz, in which it is preferable in between 5–50 Hz.

The bionic cervix uteri dilator of the present invention has the advantages of a novel structure as well as safety and reliability. With the output of a narrow pulse of frequency 1–200 Hz(being preferably selected from 5 to 150 HZ, further being preferable in between 5–50 Hz.) on the output terminal, cervix uteri can be effectively dilated by stimulating the acupoints such as the ear acupoints with the pulse, such that the treatments of gynecological diseases can be facilitated and the pains caused by cervical dilating by the use of instruments can be alleviated. The present invention is worth widely popularizing and utilizing.

What is claimed is:

1. A bionic cervix uteri dilator, comprising:
   a power supply circuit having an output terminal,
   an oscillating circuit having an input terminal and an output terminal, the input terminal being connected to the output terminal of the power supply circuit,
   a set-up transformer circuit having an input terminal and an output terminal, the input terminal being connected to the output terminal of the oscillating circuit, and curing electrodes connected to the output terminal of the step-up transformer circuit.

2. The bionic cervix uteri dilator according to claim 1, wherein a voltage output from the output terminal of the, step-up transformer circuit has a frequency in the range of 1–200 Hz.

3. The bionic cervix uteri dilator according to claim 2, wherein a voltage output from the output terminal of the step-up transformer circuit has a frequency in the range of 5–150 Hz.

4. The bionic cervix uteri dilator according to claim 3, wherein a voltage output from the output terminal of the step-up transformer circuit has a frequency in the range of 5–50 Hz.

5. A bionic cervix uteri dilator, comprising:

a power supply circuit;

an oscillating circuit connected to an output terminal of the power supply circuit, the oscillating circuit including a chip (555) having pins (1), (2), (3), (4), (5), (6), (7), and (8), resistors and capacitors, wherein pin (1) is grounded, pin (7) is connected to a resistor, pins (2) and (6) are connected in parallel with a resistor and a capacitor and are connected in parallel with each other, pins (4) and (8) are connected in parallel and are connected to an output terminal of the power supply circuit, pin (5) is grounded via a capacitor, and pin (3) is employed as an output terminal for the oscillating circuit;

a step-up transformer having an input terminal and an output terminal, the input terminal being connected to the output terminal of the oscillating circuit; and curing electrodes connected to the output terminal of the step-up transformer.

6. The bionic cervix uteri dilator according to claim 5, wherein a voltage output from the output terminal of the step-up transformer circuit has a frequency in the range of 1–200 hz.

7. The bionic cervix uteri dilator according to claim 6, wherein a voltage output from the output terminal of the step-up transformer circuit has a frequency in the range of 5–150 Hz.

8. The bionic cervix uteri dilator according to claim 7, wherein a voltage output from the output terminal of the step-up transformer circuit has a frequency in the range of 5–50 Hz.

9. A bionic cervix uteri dilator, comprising:

a microprocessor having an output terminal;

a circuit network having an input terminal and an output terminal, the input terminal being connected to the output terminal of the microprocessor;

an analog amplifier voltage step-up circuit having an input terminal and an output terminal, the input terminal being connected to the output terminal of the circuit network; and curing electrodes connected to the output terminal of the analog amplifier voltage step-up circuit.

10. The bionic cervix uteri dilator according to claim 9, wherein a voltage output from the output terminal of the analog amplifier voltage step-up circuit has a frequency in the range of 1–200 Hz.

11. The bionic cervix uteri dilator according to claim 10, wherein a voltage output from the output terminal of the analog amplifier voltage step-up circuit has a frequency in the range of 5–150 Hz.

12. The bionic cervix uteri dilator according to claim 11, wherein a voltage output from the output terminal of the analog amplifier voltage step-up circuit has a frequency in the range of 5–50 Hz.

13. A bionic cervix uteri dilator, comprising:

a power supply circuit having an output terminal, a plurality of oscillating circuits, each oscillating circuit having an input terminal and an output terminal, the input terminal being connected to the output terminal of the power supply circuit;

a plurality of step-up transformer circuits, each step-up transformer circuit having an input terminal and an output terminal, the input terminal being connected to an output terminal of one of the plurality of oscillating circuits, and a plurality of pairs of curing electrodes, each pair of curing electrodes being connected to an output terminal of one of the plurality of step-up transformer circuits.

14. The bionic cervix uteri dilator according to claim 13, wherein a voltage output from the output terminal of from least one of the step-up transformer circuits has a frequency in the range of 1–200 Hz.

15. The bionic cervix uteri dilator according to claim 14, wherein a voltage output from the output terminal of from least one of the step-up transformer circuits has a frequency in the range of 5–150 Hz.

16. The bionic cervix uteri dilator according to claim 15, wherein a voltage output from the output terminal of from least one of the step-up transformer circuits has a frequency in the range of 5–50 Hz.

17. The bionic cervix uteri dilator according to claim 13, wherein at least one of the oscillating circuits includes a chip (555) having pins (1) (2), (3), (4), (5), (6), (7), and (8), resistors and capacitors, wherein pin (1) is grounded, pin (7) is connected to a resistor, pins (2) and (6) are connected in parallel with a resistor and a capacitor and are connected in parallel with each other, pins (4) and (8) are connected in parallel and are connected to the output terminal of the power supply circuit, pin (5) is grounded via a capacitor, and pin (3) is employed as an output terminal for the oscillating circuit.

18. The bionic cervix uteri dilator according to claim 17, wherein a voltage output from the output terminal of at least one of the step-up transformer circuits has a frequency in the range of 1–200 Hz.

19. The bionic cervix uteri dilator according to claim 18, wherein a voltage output from the output terminal of at least one of the step-up transformer circuits has a frequency in the range of 5–150 Hz.

20. The bionic cervix uteri dilator according to claim 19, wherein a voltage output from the output terminal of at least one of the step-up transformer circuits has a frequency in the range of 5–50 Hz.

* * * * *